(12) United States Patent
Csiky

(10) Patent No.: US 8,070,037 B2
(45) Date of Patent: Dec. 6, 2011

(54) CIRCULAR STAPLER FOR HEMORRHOID OPERATIONS

(75) Inventor: Laszlo Csiky, Üröm (HU)

(73) Assignee: Tyco Healthcare Group, LP, New Haven, CT (US)

( * ) Notice: Subject to any disclaimer, the term of this patent is extended or adjusted under 35 U.S.C. 154(b) by 0 days.

(21) Appl. No.: 12/718,364

(22) Filed: Mar. 5, 2010

(65) Prior Publication Data

US 2010/0155452 A1    Jun. 24, 2010

Related U.S. Application Data

(62) Division of application No. 10/569,538, filed as application No. PCT/US2004/028928 on Sep. 1, 2004, now Pat. No. 7,686,201.

(30) Foreign Application Priority Data

Sep. 1, 2003  (HU) .................................. 0302804
Nov. 12, 2003 (HU) .................................. 0303705

(51) Int. Cl.
*A61B 17/068* (2006.01)
(52) U.S. Cl. ..................... 227/179.1; 227/175.1; 227/19
(58) Field of Classification Search .... 227/175.1–182.1, 227/19; 606/219, 153, 155
See application file for complete search history.

(56) References Cited

U.S. PATENT DOCUMENTS

| | | | | |
|---|---|---|---|---|
| 4,476,863 A | * | 10/1984 | Kanshin et al. ............... | 606/153 |
| 4,505,272 A | * | 3/1985 | Utyamyshev et al. ..... | 227/179.1 |
| 4,592,354 A | * | 6/1986 | Rothfuss ................... | 227/179.1 |
| 4,703,887 A | * | 11/1987 | Clanton et al. ................. | 227/19 |
| 4,817,847 A | * | 4/1989 | Redtenbacher et al. ........ | 227/19 |
| 4,917,114 A | * | 4/1990 | Green et al. .................. | 227/179.1 |
| 5,122,156 A | * | 6/1992 | Granger et al. ............... | 606/219 |
| 5,197,648 A | * | 3/1993 | Gingold ....................... | 227/179.1 |
| 5,222,963 A | * | 6/1993 | Brinkerhoff et al. ......... | 606/153 |
| 5,261,920 A | * | 11/1993 | Main et al. .................... | 606/153 |
| 5,271,543 A | | 12/1993 | Grant et al. | |
| 5,309,927 A | * | 5/1994 | Welch ........................... | 128/898 |
| 5,395,030 A | | 3/1995 | Kuramoto et al. | |
| 5,411,508 A | * | 5/1995 | Bessler et al. ................. | 606/153 |
| 5,669,918 A | * | 9/1997 | Balazs et al. .................. | 606/139 |
| 5,732,872 A | | 3/1998 | Bolduc et al. | |
| 5,860,581 A | | 1/1999 | Robertson et al. | |
| 5,902,310 A | * | 5/1999 | Foerster et al. ............... | 606/142 |
| 5,915,616 A | | 6/1999 | Viola et al. | |
| 5,964,782 A | | 10/1999 | Lafontaine et al. | |
| 6,083,241 A | | 7/2000 | Longo et al. | |
| 6,102,271 A | | 8/2000 | Longo et al. | |
| 6,117,148 A | * | 9/2000 | Ravo et al. .................... | 606/153 |
| 6,119,913 A | | 9/2000 | Adams et al. | |
| 6,203,553 B1 | | 3/2001 | Robertson et al. | |
| 6,338,737 B1 | | 1/2002 | Toledano | |
| 6,387,105 B1 | * | 5/2002 | Gifford et al. ................ | 606/139 |
| 6,959,851 B2 | | 11/2005 | Heinrich | |

(Continued)

*Primary Examiner* — Lindsay Low

(57) ABSTRACT

A circular stapler for performing hemorrhoidal operations is disclosed. The circular stapler includes an anvil, a stapler head and a shaft which movably supports the anvil in relation to the stapler head between open and closed positions. The stapler includes at least one displacing member, each of which is arbitrarily and/or independently displaceable along the shaft. Each of the at least one displacing members has a first end configured to engage a pursestring suture and a second end which extends through the body, e.g., the neck of the stapler. The displacing member is arbitrarily displaceable along the shaft. In one embodiment, two independently displaceable displacing members are provided. In another embodiment, the at least one displacing member is at least partially embedded in the shaft.

12 Claims, 4 Drawing Sheets

U.S. PATENT DOCUMENTS

| | | |
|---|---|---|
| 7,128,748 B2 * | 10/2006 | Mooradian et al. ............ 606/151 |
| 7,160,311 B2 | 1/2007 | Blatter et al. |
| 7,168,604 B2 | 1/2007 | Milliman et al. |
| 2001/0002335 A1 | 5/2001 | Yang et al. |
| 2001/0039436 A1 * | 11/2001 | Frazier et al. ................. 606/219 |
| 2004/0199182 A1 | 10/2004 | Milliman et al. |
| 2005/0059997 A1 * | 3/2005 | Bauman et al. ................ 606/219 |
| 2005/0145675 A1 * | 7/2005 | Hartwick et al. ........... 227/180.1 |
| 2005/0205640 A1 * | 9/2005 | Milliman .................... 227/176.1 |
| 2007/0023475 A1 * | 2/2007 | Csiky ......................... 227/175.1 |

* cited by examiner

CIRCULAR STAPLER FOR HEMORRHOID OPERATIONS

This application is a divisional application of application Ser. No. 10/569,538, filed on Feb. 23, 2006 now U.S. Pat. No. 7,686,201, which is a 371 national stage application of PCT/US04/28928, filed Sep. 1, 2004, which claims priority from Hungarian application Nos. P0302804,h filed Sep. 1, 2003 and P0303705, filed Nov. 12, 2003. The entire contents of each of these applications are incorporated herein by reference.

BACKGROUND

1. Technical Field

The present disclosure relates to a circular stapler for hemorrhoid operations. More specifically, the present disclosure relates to a modified circular stapler for simplifying in hemorrhoidal operations the process of pulling prolapsed hemorrhoidal and/or mucosal tissues into the stapling head.

2. Background of Related Art

A circular stapler (HCS33) has recently been made public which is suitable for hemorrhoid operations and shows extraordinarily good results. During its use, however, there arise several technical difficulties, as for example: the difficulty of pulling the suture or thread through the lateral holes of the stapler head, or the repeated knotting of the ends of the suture or thread. As a result, the instrument after having already been set, repeatedly moves out of place or temporarily releases.

Accordingly, there has arisen a need for a modified circular stapler which eliminates the above-mentioned technical difficulties which occur during hemorrhoidal operations.

SUMMARY

In accordance with the present disclosure and on the basis of the above-mentioned recognition, a modified circular stapler is disclosed which can include a ring, a displacing tube or one or more displacing rods with hooks or holes that can be independently or arbitrarily moved along a shaft of the stapler. The shaft of the stapler connects the anvil to the stapler head and may include a pin attached to the anvil and a sheath movably attached to the stapler head.

In accordance with a first embodiment of the presently disclosed circular stapler, a ring which has an arbitrarily fashioned flange and a connectable rim is attached to the pin of the anvil. The ring is freely movable along the shaft of the pin and sheath. A displacing tube surrounds the sheath and has at its upper end a hangable hook that can be connected to the attaching rim and at its lower end a displacing button. Through the body, e.g., the head, neck or handle, of the stapler, there is a slot which is arranged longitudinally and in which the displacing button moves. As another possible solution, the displacing tube may be replaced by a displacing rod that is provided with a hangable hook that can be connected to the connecting rim.

In accordance with a second embodiment of the presently disclosed circular stapler, the pin and sheath are fixed by an insoluble connection and, thus, define an integral shaft. The displacing tube forms a rigid unit with the ring and is freely movable along the shaft. A displacing button is connected to the lower end of the displacing tube. On the neck of the stapler, there is a slot which runs longitudinally and has arranged at its upper end a lateral slot portion which locks the displacing button in place. According to another possible solution, the displacing tube may be replaced by a displacing rod.

In accordance with a third embodiment of the presently disclosed circular stapler, a thread or wire with a circlet is connected to the ring that is freely movable along the shaft. The neck of the stapler contains a hole through which the thread or wire exits the neck.

In accordance with a fourth embodiment of the presently disclosed circular stapler, a displacing rod is or a plurality of displacing rods are provided. Each displacing rod includes a hole or a hook at an upper end thereof. On the neck of the stapler, there is a slot that runs longitudinally and can include a lateral component which locks the displacing button in place. As a possible advantageous solution, the one or more displacing rods may be at least partially embedded into the unitarily cast shaft of the pin and sheath.

BRIEF DESCRIPTION OF THE DRAWINGS

Various embodiments of the presently disclosed circular stapler for hemorrhoid operations are disclosed herein with reference to the drawings, wherein.

DETAILED DESCRIPTION OF EMBODIMENTS

Figure 1:
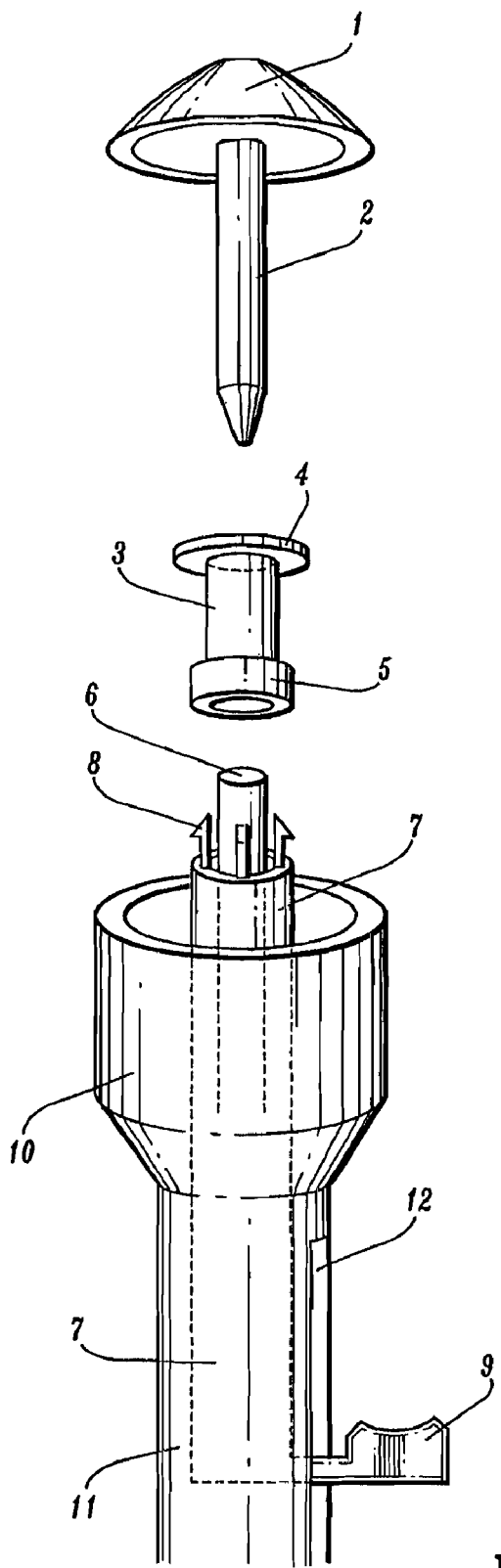
FIG. 1 is a side elevational view with parts separated of the distal portion of one embodiment of the presently disclosed circular stapler.

Embodiments of the presently disclosed circular stapler will now be described in detail with reference to the drawings in which like reference numerals designate identical or corresponding elements in each of the several views.

Referring to FIG. 1, the presently disclosed circular stapler includes an anvil 1 and a stapling or stapler head 10. Anvil 1 is movably supported in relation to stapler head 10 in a known manner between open and closed positions. Stapler head 10 supports a plurality of staples (not shown). The stapler is operable in a known manner to eject the staples from stapler head 10 into or against anvil 1. The stapler also includes a knife (not shown) which is movable in a known manner from within stapler head 10 towards anvil 1 to cut tissue positioned between anvil 1 and stapler head 10.

Figure 1A:
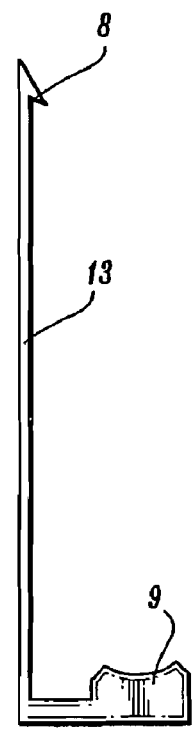
FIG. 1A is a side elevational view of a displacing rod having a connecting component and button of the circular stapler shown in FIG. 1.

As can be seen in FIG. 1, a ring 3 can be slid freely along the disassemblable shaft that includes a pin 2 of anvil 1 and a sheath 6 of stapler head 10. The disassemblable shaft connects anvil 1 to the stapler. At the upper edge of ring 3 there is an arbitrarily arrangeable flange 4 which is used to hang up or engage a purse-string suture. At a lower edge of ring 3 there can be a connectable rim 5 which makes it possible to connect ring 3 to a displacing member, e.g., a connectable displacing tube 7 or a displacing rod 13. Displacing tube 7 is situated outside sheath 6. At the upper end of displacing tube 7 or the displacing rod 13, there is a hangable hook 8. At a lower end of displacing tube 7 or displacing rod 13, there is a displacing button 9. On neck 11 of the stapler there is a slot 12 which is longitudinally arranged. FIG. 1A shows displacing rod 13 having displacing button 9 on a proximal end and a connecting component in the form of a hangable hook 8 on a distal end.

Figures 2, 2A:
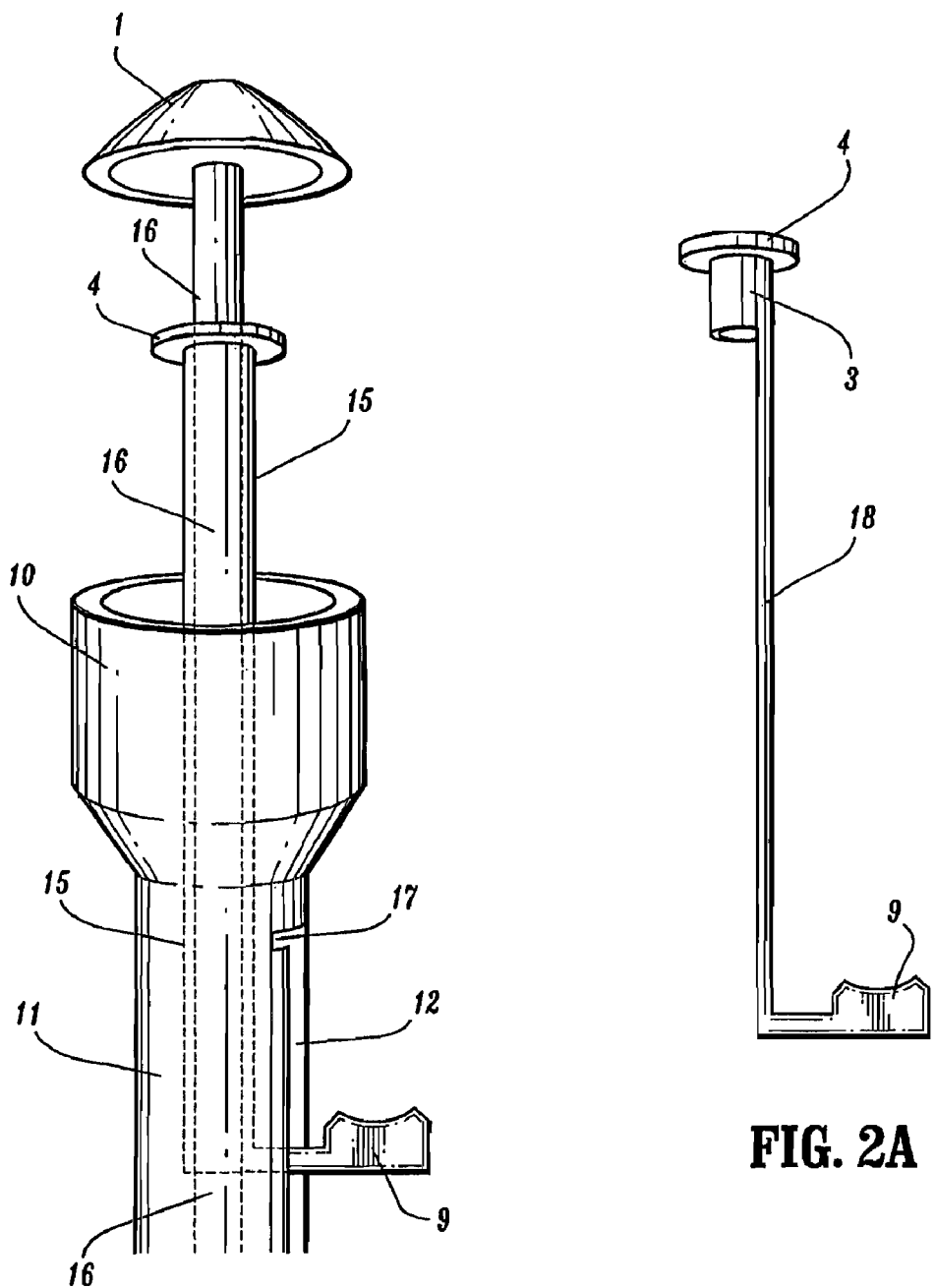
FIG. 2 is a side elevational view of the distal portion of a second embodiment of the presently disclosed circular stapler.
FIG. 2A is a side elevational view of a displacing rod having a ring and button of the circular stapler shown in FIG. 2.

As can be seen in FIG. 2, the pin and the sheath are integrally formed as a shaft 16 which is not disassemblable. Shaft 16 is surrounded by an independent displacing tube 15, at whose lower end is displacing button 9 and at whose upper end is flange 4. The displacing tube or displacing rod forms a rigid unit with the ring and surrounds shaft 16. The upper end of longitudinal slot 12 is arranged on neck 11 of the stapler and includes an angled continuation which forms a locking slot 17 for receiving displacing button 9. FIG. 2A shows displacing rod 18, which forms a rigid unit with ring 3.

Figure 3:
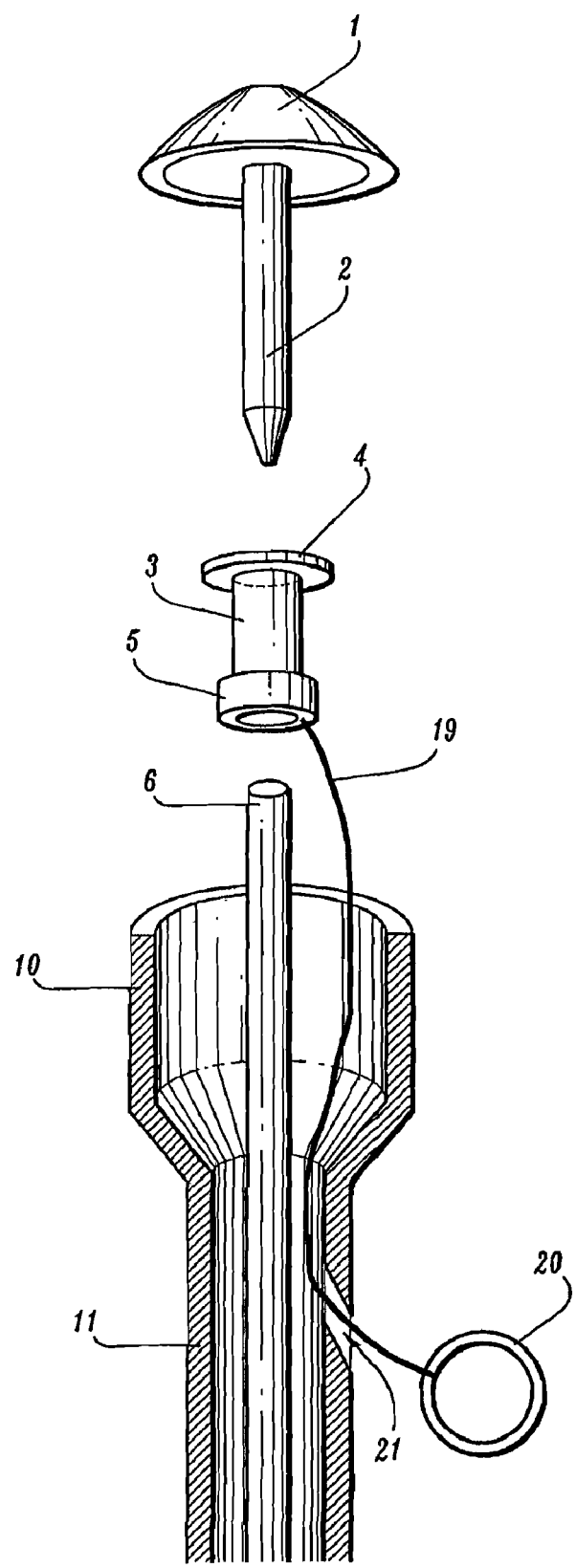
FIG. 3 is a side elevational, partial cross-sectional view with parts separated of the distal portion of a third embodiment of the presently disclosed circular stapler.

As can be seen in FIG. 3, a displacing member including a thread or wire 19 at its proximal end having a circlet 20 can be connected to ring 3, which is freely movable along the disassemblable shaft defined by pin 2 and sheath 6. On neck 11 of the stapler, there is arranged through a hole 21 through which thread or wire 19 extends from neck 11 and is movable.

Figure 4:
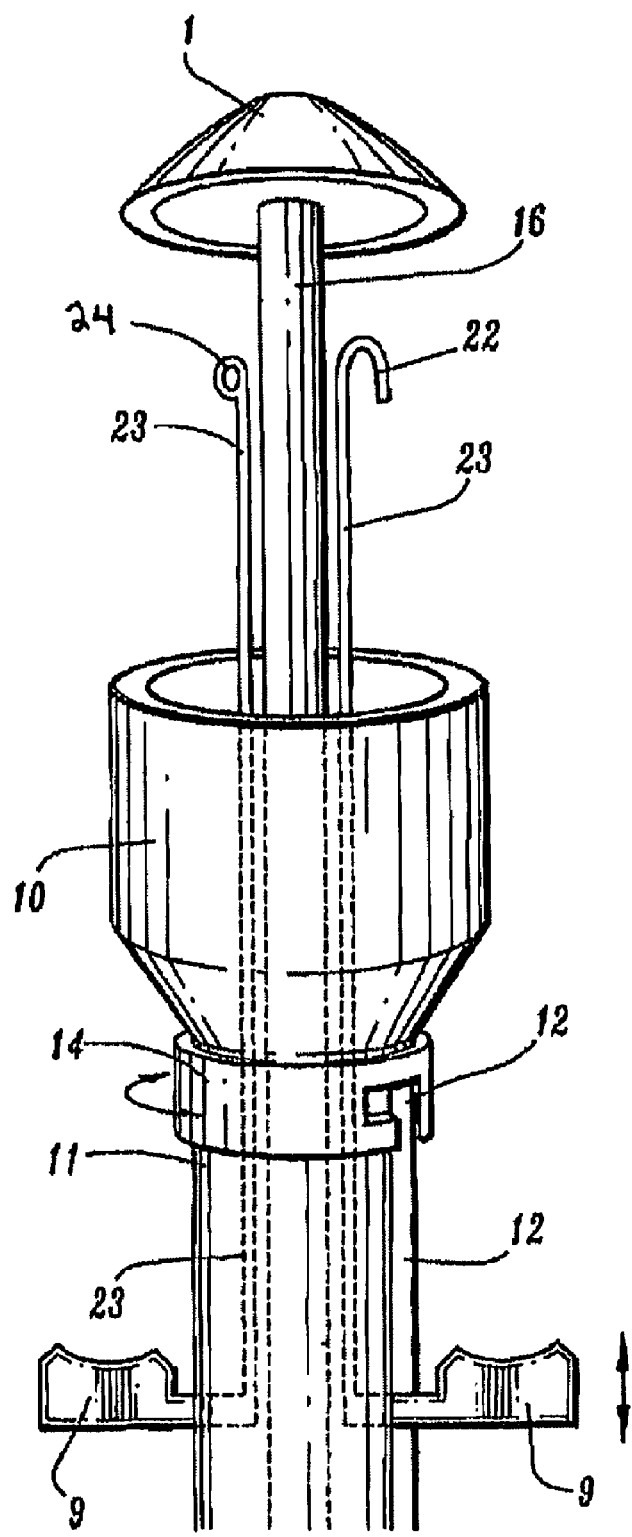
FIG. 4 is a side, elevational view of the distal portion of a fourth embodiment of the presently disclosed circular stapler.
Figure 4B:
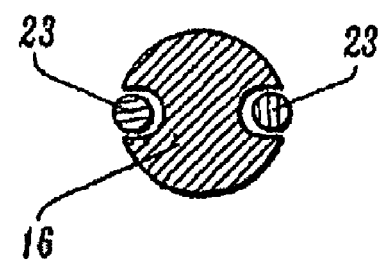
FIG. 4B is a cross-sectional view as would be seen through the shaft with displacing rods slidably mounted or embedded therein according to another alternate embodiment of the circular stapler shown in FIG. 4.
Figure 4A:
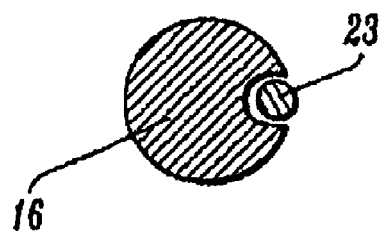
FIG. 4A is a cross-sectional view as would be seen through the shaft with displacing rods slidably mounted or embedded therein according to an alternate embodiment of the circular stapler shown in FIG. 4.

As can be seen in FIG. 4, the pin and the sheath are formed as an integral shaft 16 which is not disassemblable. Ring 3 is replaced by one or more or motive sticks or displacing rods 23, each of which is provided with a hook 22 or advantageously with a hole 24. At a lower end of each displacing rod 23, there is a displacing button 9. Displacing rod 23 runs beside shaft 16 or, alternatively, is slidably embedded into shaft 16 (FIG. 4A). Longitudinal slot 12 is arranged on neck 11 of the stapler and has at its upper end a component 14 which is rotatable about neck 11 to lock displacing button 9 in a position in relation to neck 11. Displacing button 9, together with displacing rod 23, can be arbitrarily moved in slot 12.

The operation of the mechanism in accordance with the invention is the following:

After placing an inner purse-string suture in the rectum, anvil 1 is introduced into the rectum. Anvil 1 can be dish-shaped. Ring 3 slides freely on pin 2 of anvil 1. The purse-string suture is fixed with a knot to or on the body of ring 3 under arbitrarily arrangeable flange 4. Next, pin 2 is connected to sheath 6 and displacing tube 7 is connected to connecting rim 5 using the hangable hooks 8. Alternately, displacing tube 7 may be replaced by the displacing rod 13. Prior to operation, displacing button 9 is positioned at the upper end of slot 12. Displacing button 9 can now be pulled downward to pull the hemorrhoidal tissues attached by the purse-string suture to ring 3 downward, into the interior of stapling head 10. Next, the stapler can be closed and actuated in a manner which in and of itself is well known.

According to another possible solution, thread or wire 19 having a ring or circlet 20 is connected to ring 3 (See FIG. 3). Thread 19 is pulled through hole 21 arranged on neck 11 of the stapler, to pull down ring 3 together with the hemorrhoidal tissues attached thereto via the purse-string suture.

Insofar as the stapler has unified shaft 16 for the pin and sheath, an independent displacing tube 15, or a displacing rod 18 which forms a rigid unit with ring 3 can be used. Displacing button 9 can be placed into locking slot 17 or locked by means of locking component 14 (which may advantageously be a rotatable ring), while the head 10 of the stapler is pushed or inserted into the rectum and the knot of the suture is positioned under flange 4 of ring 3. After this, displacing button 9 is moved into longitudinal slot 12, or locking component 14 is rotated to unlock displacing button 9. Displacing button 9 can now be pulled downward. The remainder of the procedure is similar to what has been described above. As a possible variation, instead of using ring 3, a displacing rod 23 which at its end is provided advantageously with a hole 24 and/or with a hook 22. Its use is similar to what has been described above, i.e., the purse-string suture is fixed through hole 24 or under the hook 22. Displacing rod 23 is positioned along or beside shaft 16. Alternately, displacing rod 23 may be embedded into shaft 16 (FIG. 4A).

Insofar as the stapler has a plurality of displacing rods 23, e.g., two such rods, two half purse-string sutures independent of each other can be attached to the ends of the two separate displacing rods 23, each of which is provided with a hole 24 or a hook 22. As such, there is obtained the possibility of pulling displacing rods 23 to different degrees to pull the prolapsed hemorrhoidal cushion portions that have become loosened to different degrees into stapler head 10 and thereby facilitate and obtain differentiated excision of the different hemorrhoidal cushioned portions. The displacing rods 23 can be pulled different distances to provide an excision which is proportional to the loosening of the respective hemorrhoidal tissue portions.

An important advantage of the solutions in accordance with an embodiment or embodiments of the invention is that in the event of hemorrhoidal operations using a stapler of the invention, it ensures that the operating technology or technique is simplified, that the instrument's moving out of place or releasing is eliminated, and that the excision will be proportional to the loosening of the respective hemorrhoidal tissues.

What is claimed is:

1. A circular stapler for performing hemorrhoidal operations, the stapler comprising:
   an anvil and a stapler head, the anvil being supported on a shaft and being movable in relation to the stapler head between open and closed positions, the stapler including a ring which is arbitrarily displaceable along the shaft, the ring being configured, dimensioned, and adapted such that proximal movement of the ring draws tissue into the stapler head, and a displacing member having a first end connected to the ring and a second end extending through a body of the stapler such that at least a portion of the second end of the displacing member is positioned externally of the body of the stapler to facilitate movement of the displacing member to arbitrarily displace the ring along the shaft, wherein the body of the stapler includes a longitudinal slot, the second end of the displacing member extending through the longitudinal slot such that the longitudinal slot guides movement of the displacing member, and wherein the stapler includes a locking slot for locking the displacing member in a fixed position.

2. A circular stapler as recited in claim 1, wherein the displacing member includes a displacing rod.

3. A circular stapler as recited in claim 1, wherein the displacing member includes a displacing tube.

4. A circular stapler as recited in claim 1, wherein the displacing member is provided with a displacing button.

5. A circular stapler as recited in claim 1, wherein the displacing member forms a rigid unit with the ring.

6. A circular stapler for performing hemorrhoidal operations, the stapler comprising:
an anvil, a stapler head and a body that communicates with the stapler head, the anvil being supported on a shaft and being movable in relation to the stapler head between open and closed positions, wherein the stapler includes a ring which is arbitrarily displaceable along the shaft, and a displacing member including a thread or wire having a first end secured to the ring and a second end extending through the body of the stapler, the displacing member being movable to arbitrarily displace the ring along the shaft, the ring being configured, dimensioned, and adapted such that proximal movement of the ring draws tissue into the stapler head.

7. A circular stapler as recited in claim 6, wherein the shaft includes a pin which is attached to the anvil and a sheath which is movably supported on the stapler, the pin being dissassembleable from the sheath.

8. A circular stapler as recited in claim 6, wherein the ring includes a flange and a connecting rim.

9. A circular stapler as recited in claim 6, wherein the body of the stapler includes a hole and the displacing member extends through the hole.

10. A circular stapler for performing hemorrhoidal operations, the stapler comprising:
an anvil and a stapler head, the anvil being supported on a shaft and being movable in relation to the stapler head between open and closed positions, wherein the stapler includes at least one displacing rod, each of the at least one displacing rods having a first end provided with a hole or hook configured to engage a suture and a second end extending through a body of the stapler, wherein the stapler includes a rotatable locking component for locking the displacing rod in a fixed position.

11. A circular stapler for performing hemorrhoidal operations, the stapler comprising:
an anvil and a stapler head, the anvil being supported on a shaft and being movable in relation to the stapler head between open and closed positions, wherein the stapler includes at least one displacing rod, each of the at least one displacing rods having a first end provided with a hole or hook configured to engage a suture and a second end extending through a body of the stapler, wherein one or more of the displacing rods at least partially embedded in the shaft.

12. A circular stapler as recited in claim 1, wherein the second end of the displacing member is configured and dimensioned for manual engagement.

* * * * *